United States Patent [19]

Mulder et al.

[11] Patent Number: 5,106,383
[45] Date of Patent: Apr. 21, 1992

[54] CLOSURE SYSTEMS FOR DIAPERS AND METHOD OF PREPARATION

[75] Inventors: Robert S. Mulder, Eagan; Douglas A. Swenson, St. Paul, both of Minn.

[73] Assignee: Minnesota Mining and Manufacturing Company, St. Paul, Minn.

[21] Appl. No.: 387,606

[22] Filed: Jul. 28, 1989

[51] Int. Cl.⁵ .............................................. A61F 13/15
[52] U.S. Cl. ..................................... 604/389; 604/390
[58] Field of Search ................ 604/389, 390; 428/327, 428/412; 156/272.2, 272.6, 273.1, 273.3; 430/215

[56] References Cited

U.S. PATENT DOCUMENTS

| | | | |
|---|---|---|---|
| 2,532,011 | 11/1950 | Dahlquist et al. | 154/53.5 |
| 3,632,386 | 1/1972 | Hurst | 117/46 FC |
| 3,867,940 | 2/1975 | Mesek et al. | 128/287 |
| 4,210,144 | 7/1980 | Sarge et al. | 128/287 |
| 4,296,750 | 10/1981 | Woon et al. | 128/287 |
| 4,429,032 | 1/1984 | Matthe et al. | 430/215 |
| 4,539,256 | 9/1985 | Shipman | 428/315.5 |
| 4,609,584 | 9/1986 | Cutler et al. | 428/156 |
| 4,643,730 | 2/1987 | Chen et al. | 604/390 |
| 4,710,190 | 12/1987 | Wood et al. | 604/389 |
| 4,726,989 | 2/1988 | Mrozinski | 428/315.5 |
| 4,753,649 | 6/1988 | Pazdernik | 604/389 |

OTHER PUBLICATIONS

D. Briggs, Surface Treatments for Polyolefins, D. M. Brewis, Ed., MacMillan, N.Y., 1982 Chapter 9, pp. 199-226.

*Primary Examiner*—Randall L. Green
*Assistant Examiner*—R. Clarke
*Attorney, Agent, or Firm*—Gary L. Griswold; Walter N. Kirn; Carole Truesdale

[57] ABSTRACT

A disposable article, such as a disposable diaper, is provided. The article has a fastening means comprising a film substrate having a target strip and a fastening tape. The target strip comprises a backing film having a first pressure-sensitive adhesive on one face thereof adhered to the film substrate and on the other face thereof a hydrophobic polyvinyl carbamate release coating. The fastening tape has a second pressure-sensitive adhesive on one face thereof for adhesion to the target strip. The target strip release coating has been subjected to ionizing plasma treatment such that the fastening tape has an increase in adhesion to the target strip of at least about 50% over an untreated target strip and which increased adhesion does not decrease more than 60% after storage at about 50° C. for 15 days.

15 Claims, 2 Drawing Sheets

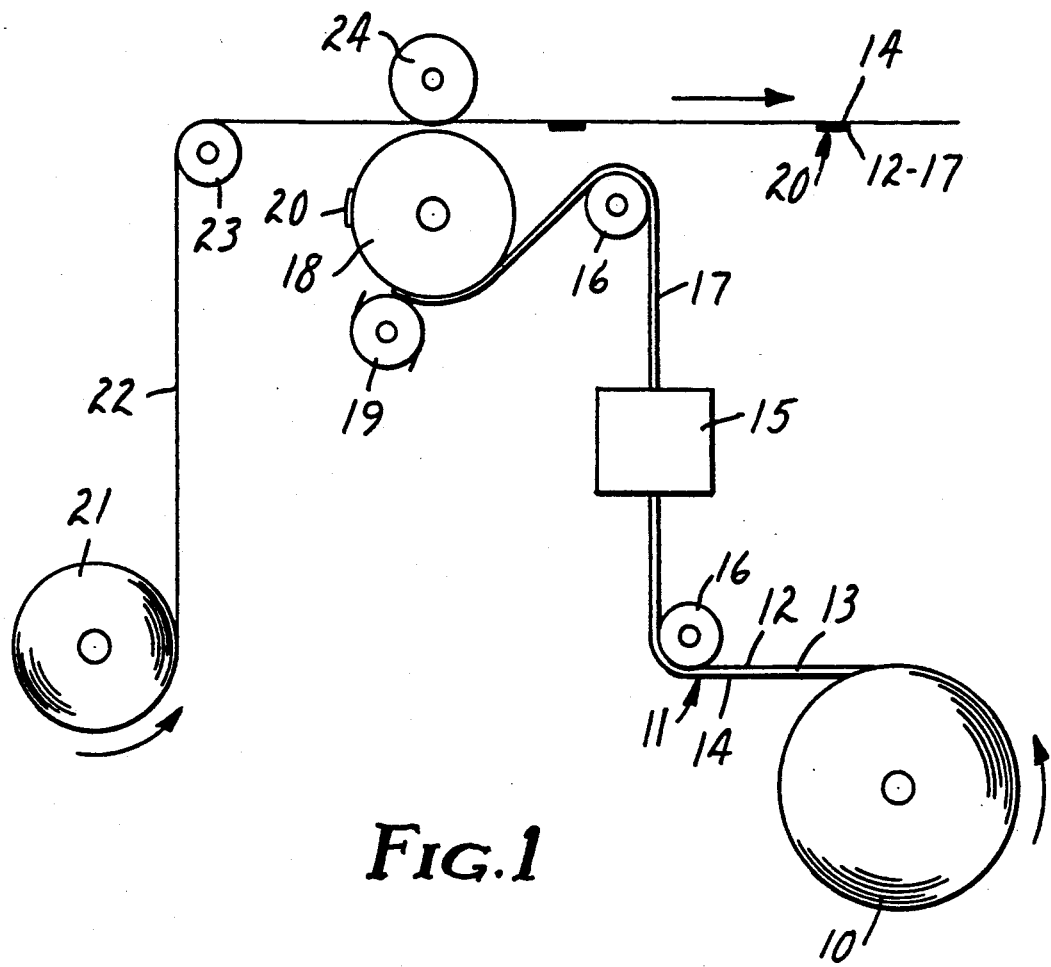
FIG.1
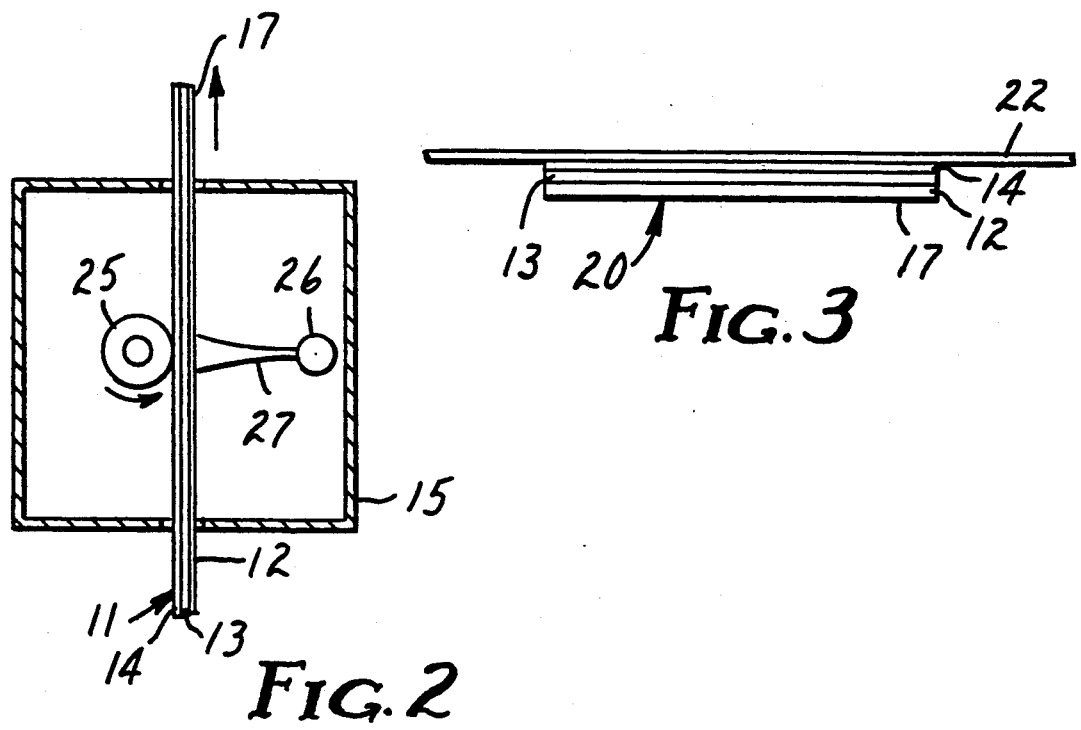
FIG.2
FIG.3

CLOSURE SYSTEMS FOR DIAPERS AND METHOD OF PREPARATION

BACKGROUND OF THE INVENTION

1. Field of the Invention

This invention relates to a refastenable closure system for disposable garments, such as disposable diapers, and the method for preparing disposable garments with this improved closure system.

2. Background Information

Disposable diapers are generally comprised of a liquid-permeable inner skin-contacting layer, a liquid impermeable outer layer, and an absorbent layer disposed between these inner and outer layers. The inner layer can be a nonwoven or other soft liquid-permeable material. Nonwoven materials of polyolefin-based fibers are particularly useful as the inner layer. The absorbent layer can be formed of cellulosic fibers, polyolefin-based nonwoven webs which can contain absorbent particulate materials, or like materials. The outer layer of disposable diapers can be liquid-impermeable polyolefin-based films, preferably with a matte or embossed surface. The outer layer can be a polyolefin-based microporous film which is impermeable to liquids but permeable to gases, such as the polyolefin-based films described in U.S. Pat. Nos. 4,593,256 (Shipman), No. 4,609,584 (Cutler et al.), and No. 4,726,989 (Mrozinski).

A disposable diaper typically includes a closure system for securing the diaper about the wearer. This closure system typically comprises pressure-sensitive adhesive fastening tape tabs which are adhered to the marginal edges of the diaper, near one end, in the waist area of the diaper, in such a manner that a portion of each tab is free for use to adhere to the outer layer of the diaper at the opposite end to secure the diaper about the wearer. It is desirable that the closure formed by these pressure-sensitive adhesive fastening tape tabs be quite secure, to avoid unwanted opening of the closure. However, it is also desirable that the closure be capable of being repeatedly opened and reclosed, i.e., be refastenable, to allow for adjusting the fit of the diaper or for checking for a soiled condition.

The outer layer of a disposable diaper preferably comprises a polyolefin based film. In the interest of economy and to minimize stiffness of the diaper it is desirable that this outer layer be a thin film, typically in the range of 20 to 40 microns thick. As such, these films are of limited strength and this limited strength can be a limiting factor on how secure a closure can be formed and remain functionally refastenable. An aggressive pressure-sensitive adhesive fastening tape tab can distort or tear these thin film outer layers when the closure is opened, thus destroying the functionality of the closure system. To overcome this problem, various techniques have been proposed for reinforcing the outer layer in the area where the pressure-sensitive adhesive fastening tape tabs are adhered to secure the diaper about the wearer.

Various techniques are known in the art for reinforcing the outer impermeable film of disposable diapers. One technique involves coating the film with a reinforcing material either on the inner or outer surface of the film. U.S. Pat. No. 4,296,750 (Woon et al.) discloses coating the interior surface of the outer impermeable film with a hot-melt adhesive layer which has both a Ring and Ball softening point lower than that of the film and a modulus of elasticity lower than that of the film. U.S. Pat. No. 4,210,144 (Sarge III et al.) discloses a material having high tensile strength and a low elongation to tensile force property, relative to the outer impermeable film, coated on the outer impermeable film, preferably on the inner surface of the film, to both bond the film to the absorbent pad of the diaper and to reinforce the film. Problems with this technique include the cohesive strength of the coatings, which can be too low to allow lasting and complete holding of an adhesive fastening tape pressed against it; the heat of the hot-melt adhesives which can distort the thin polyolefin film during the coating process; and variations in the thickness of the coatings which can result in non-uniform reinforcement.

Another technique for reinforcing the outer layer of disposable diapers involves adhering a plastic strip to the area of the diaper to which the fastening tape is adhered to fasten the diaper around the wearer. U.S. Pat. No. 3,867,940 (Mesek et al.) discloses water-impervious backing sheets reinforced against stretching and rupture by having adhered to a minor portion of the surface thereof a flexible structural material having a higher modulus of elasticity than said backing sheet, wherein the flexible reinforcing structural material may be a scrim, such as a cotton gauze, or polyethylene filaments, or film material such as biaxially oriented polyethylene terephthalate, which can be bonded to the water-impermeable sheet by known methods, or if plyethylene gauze is used, by heat and pressure. European Patent Publication No. 0,080,647 (Boussac Saint Freres) discloses a plastic strip such as a smooth-surfaced polypropylene strip adhered to the impermeable film by a layer of adhesive. German Offenlegungsschrift No. 33 38 201 A 1 (Molnlycke) discloses a plastic strip of preferably polyethylene or polypropylene or polyester firmly adhered to the impermeable film. U.S. Pat. No. 4,753,649 (Pazdernik) discloses an article including an adhesive tape tab and a reinforced substrate in which the substrate is reinforced by bonding a reinforcing layer to the substrate wherein the reinforcing layer has a matte finish and a tensile strength of at least about 15 MPa and the reinforcing layer provides a peel force of at least about 11.7 N per inch of adhesive tab width when adhered to the adhesive tab.

In commercial practice, the above methods involve reinforcing a substrate, e.g. the outer layer of a disposable diaper, with a plastic strip, and the plastic strip is generally bonded to the substrate by one of two basic methods. One of these methods involves the reinforcing strip being provided from a roll of pressure-sensitive adhesive tape. While this method has the advantage of being a convenient method of bonding to the substrate, it also has a significant disadvantage in that to allow a uniform low-force unwinding of the adhesive-coated plastic reinforcing strip from a storage roll, the top surface of the reinforcing strip, i.e., the surface which becomes the target area to which the fastening tape is adhered in fastening the garment about the wearer, is typically coated with a release coating, thereby minimizing adhesion between the adhesive layer and the top surface. However, minimizing adhesion to the target area where the fastening tape is to be adhered is contrary to an intended characteristic of the target area, i.e., the characteristic of providing a surface to which the fastening tape can be reliably and lastingly adhered while still being capable of being peeled off of the target area without damage to the reinforcing layer or the reinforced substrate to allow for multiple closings and openings of the closure system.

The other method involves coating the plastic film with an adhesive on the manufacturing lines, for example diaper manufacturing lines, and using this adhesive to achieve the bond between the substrate and the reinforcing strip. This method does not require a release coating on the top surface of the reinforcing film as no such release coating is required to allow a roll of film to readily unwind. However, as with the methods which involve coating hot-melt adhesives onto the substrate there are several disadvantages associated with this method of achieving a reinforced substrate. These disadvantages include the complexity of such coating operations on high speed manufacturing lines, such as diaper manufacturing lines, difficulty in achieving a uniform coating, and difficulty in coating the adhesive to the edges of the reinforcing film.

One way of achieving a reinforced substrate closure system for disposable diapers which eliminates the use of a release coating while avoiding coating hot-melt adhesives on the manufacturing lines is found in U.S. Pat. No. 4,710,190 (Wood et al.) which discloses the use of a bilayer film as a reinforcing film for the outer layer of disposable diapers. The bilayer film comprises a reinforcing layer and a room-temperature-nontacky bonding layer, which is bonded to the outer layer of the diaper with heat and pressure. The reinforcing layer is free of release treatments on its top surface yet supply rolls of the bilayer film do not resist uniform low-force unwinding due to the nontacky nature of the bonding layer at room temperature. Although the use of such bilayer films overcomes the problems cited above it also suffers from the disadvantage of requiring the modification of diaper manufacturing lines to include a means for heating the bonding layer of the bilayer film, to affix pieces of this bilayer film to the substrate which forms the outer surface of the disposable diapers.

Another technique for reinforcing substrates is found in U.S. Pat. No. 4,643,730 (Chen et al.) which discloses coating at least a portion of the surface of the substrate with a layer of material that is curable by high energy radiation and curing the coating with a suitable source of high energy radiation to form a reinforced layer affixed to the substrate. The coating compositions disclosed include urethane acrylate oligomers, acrylated acrylic oligomers, and epoxy acrylate oligomers. The radiation sources disclosed include ultraviolet radiation sources and electron beam sources. The problems associated with this technique include the complexity of the method which can potentially reduce the efficiency of manufacturing lines, such as diaper manufacturing lines, the potential for non-uniform reinforcement as a result of non-uniform coatings, the relatively high cost of the materials, the potential for unpleasant odor of the uncured compositions due to low molecular weight components, and the potential for residual odor of the cured coatings due to incomplete cure.

Subjecting films to ionizing plasmas, such as produced by electrical discharge corona or flame, is well known in the art to provide an increase in the adhesion, to the film of various types of coatings which might be applied to the films as well as the adhesion of pressure-sensitive adhesive tapes. (See D. Briggs, *Surface Treatment for Polyolefins*, D. M. Brewis, Ed., MacMillan N.Y. 1982, Chapter 9, pp. 199-226.) A similar result has been reported for silicone release coatings when treated with a corona electrical discharge. U.S. Pat. No. 3,632,386 (Hurst) discloses that by subjecting a silicone polymer release surface to "oxidative" treatment, e.g., electrical discharge (corona) or flame treatment, the release properties of the surface are reduced, e.g., made more difficult. Hurst also discloses that the effect of this oxidative treatment, that of decreasing release properties of a silicone polymer release surface, is temporary unless the treated surface is protected after treatment, for example by coating the treated surface with an adhesive.

SUMMARY OF INVENTION

The present invention provides a disposable article having a fastening means comprising a film substrate having a target strip and a fastening tape, said target strip comprising a backing film having a pressure-sensitive adhesive on one face thereof adhered to the film substrate and on the other face thereof a hydrophobic polyvinyl carbamate release coating, said fastening tape having a pressure-sensitive adhesive on one face thereof for adhesion to the target strip, the target strip release coating having been subjected to ionizing plasma treatment such that the fastening tape has an increase in adhesion to the target strip of at least about 50%, more preferably at least about 100%, over an untreated target strip and which increased adhesion does not decrease more than about 60%, preferably about 40%, more preferably about 20%, after storage at 50° C. for 15 days. The disposable articles of the present invention include, for example, disposable diapers, incontinence garments, disposable gowns, and the like.

The present invention also provides a method for producing disposable articles comprising the steps of
(a) unwinding a pressure-sensitive adhesive reinforcing tape having a polymeric backing sheet material bearing a pressure-sensitive adhesive on one side of said backing sheet material and a hydrophobic polyvinyl carbamate release coating on the other side of said backing sheet material;
(b) exposing said release coating to ionizing plasma;
(c) cutting said reinforcing tape into target strips;
(d) providing a substrate sheet material; and
(e) adhering said pressure-sensitive adhesive bearing side of said target strips to said substrate,
said exposed release coating having an increase in adhesion to pressure-sensitive adhesive of at least about 50% over an untreated target strip and which increased adhesion does not decrease more than 60% after storage at 50° C. for 15 days.

The present invention further provides a disposable diaper comprising a porous facing layer to be positioned adjacent an infant's skin, an absorbent batt, a water-impervious backing sheet having a target strip and a fastening tape, said target strip comprising a backing film having a first pressure-sensitive adhesive on one face thereof adhered to the film substrate and on the other face thereof a release coating of hydrophobic polyvinyl carbamate, said fastening tape having a second pressure-sensitive adhesive on one face thereof for adhesion to the target strip, the target strip release coating having been subjected to ionizing plasma treatment such that the fastening tape has an increase in 135° peel adhesion to the target strip of at least about 50% over an untreated target strip and which increased adhesion does not decrease more than 60% after storage at about 50° C. for 15 days.

BRIEF DESCRIPTION OF THE DRAWINGS

FIG. 1 is a schematic view showing a portion of an apparatus for producing disposable articles in accordance with one aspect of the invention.

FIG. 2 is a schematic view of the ionizing radiation producing portion of the apparatus of FIG. 1.

FIG. 3 is a cross-sectional view of a portion of a disposable article in accordance with one aspect of the invention.

DETAILED DESCRIPTION OF THE INVENTION

Figure 4:
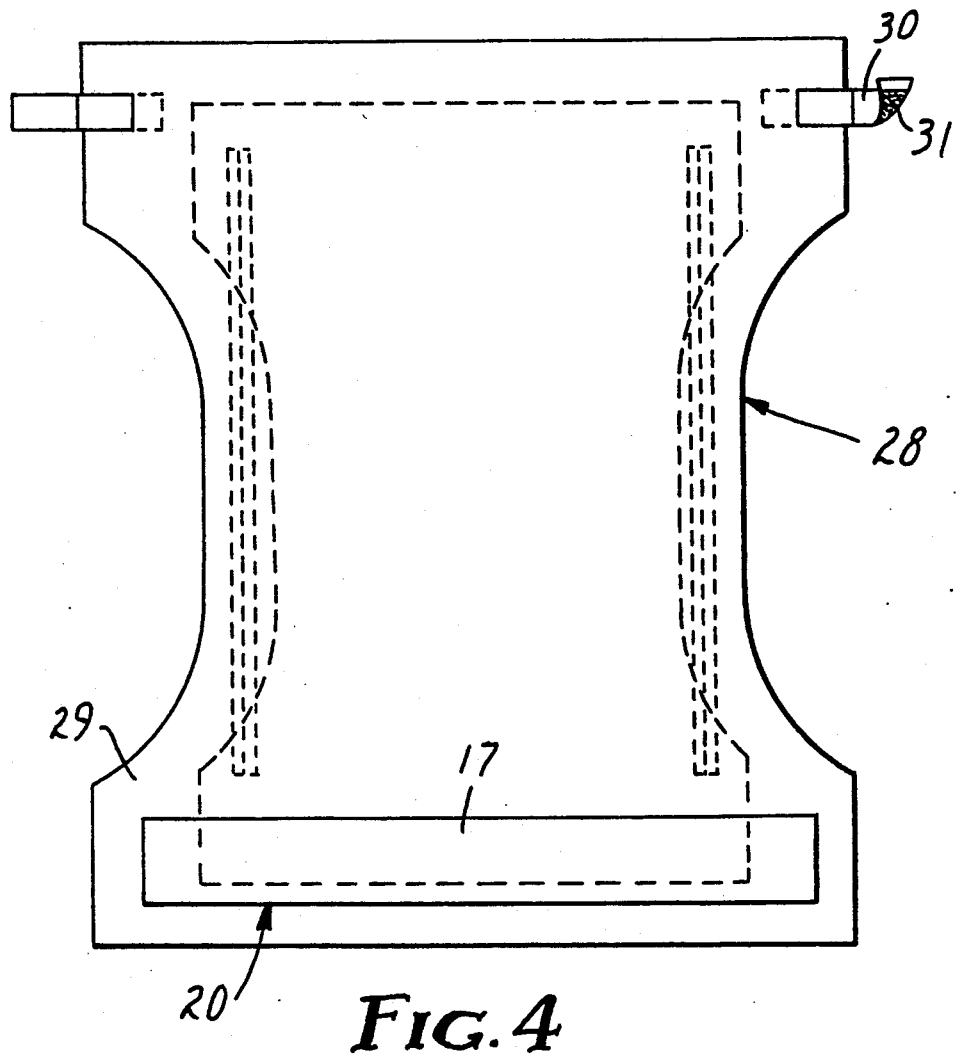
FIG. 4 is top view of a disposable diaper in accordance with one aspect of the invention.

The backing film useful in the target strip of the present invention can be formed from thermoplastic materials such as polyester, polyethylene, polypropylene, copolymers of propylene and ethylene, and like materials. The backing film is preferably a biaxially oriented polypropylene film or a non-oriented polypropylene film and preferably has matte surfaces. The backing film is preferably between about 20 and 50 micrometers thick.

The pressure-sensitive adhesive of the target strip can be any pressure-sensitive adhesive which forms an aggressive adhesive bond to polyolefin substrates such as are used as the outer layer of disposable diapers. Examples of the types of adhesives suitable for use include those based on tackified natural and synthetic rubbers. Particularly preferred are tackified synthetic rubbers which are block copolymer elastomers such as AB block copolymers wherein A comprises a polymerized vinylarene, B comprises a polymer of at least one monomer selected from conjugated dienes and alkenes, and A preferably comprises from 8 to 50 weight percent of the block copolymer.

Useful materials for the release coating of the target strip are hydrophobic polyvinyl carbamates. Particularly useful materials are hydrophobic polyvinyl carbamates having nitrogen bonded hydrocarbon side chains which provide terminal alkyl groups of more than five carbon atoms in length, as disclosed in U.S. Pat. No. 2,532,011, which is hereby incorporated by reference. The release coating most preferably is polyvinyl N-octadecyl carbamate. The release coating is preferably present in an amount of about 0.02 to 1.2 $g/m^2$, more preferably about 0.05 to 0.5 $g/m^2$, most preferably about 0.1 to 0.4 $g/m^2$.

The adhesion of pressure-sensitive adhesive fastening tape tabs to the release coatings of the target strips of the present invention, after exposure to an ionizing plasma, is preferably increased at least 50 percent over adhesion prior to exposure to ionizing radiation. When the backing film is biaxially oriented polypropylene, the adhesion is preferably greater than about 400 grams per 2.54 cm of width, and more preferably greater than about 600 grams per 2.54 cm of width, of the fastening tape, both initially and after storage at 50° C. for 15 days after exposure of the release coating of the target strip to an ionizing plasma. When the backing film is cast polypropylene, the adhesion is preferably greater than about 600 grams per 2.54 cm of width, and more preferably greater than about 800 grams per 2.54 cm of width, of the fastening tape, both initially and after storage at 50° C. for 15 days after exposure of the release coating of the target strip to an ionizing plasma.

The pressure-sensitive adhesive fastening tape of the present invention comprises a backing film with a pressure-sensitive adhesive layer on one surface and, optionally, a release coating on the other surface. Preferably, the backing film is a polyolefin film. The pressure-sensitive adhesive of the fastening tape can be any pressure-sensitive adhesive which forms an aggressive adhesive bond to polyolefin substrates and the ionizing plasma treated release coating of the target strip. Examples of the types of adhesives suitable for use include those based on tackified natural and synthetic rubbers. Particularly preferred are tackified synthetic rubbers which are block copolymer elastomers such as AB block copolymers wherein A comprises a polymerized vinylarene, B comprises a polymer of at least one monomer selected from conjugated dienes and alkenes, and A comprises from 8 to 50 weight percent of the block copolymer.

The present invention provides disposable garments with fastening means that have the high closure forces that can be achieved with target strips that do not have a release coating but maintains the convenience of using a self-wound roll of pressure-sensitive adhesive reinforcing tape as the source of the target strips. In the disposable garments of the present invention although the pressure-sensitive adhesive fastening tape tabs can form an aggressive adhesive bond to the ionizing plasma treated release coating of the target strips, thus forming a secure closure, the closure can be repeatedly opened and reclosed by peeling the fastening tape tabs from the reinforcing tape without distorting or tearing the reinforcing tape or the outer layer of the garment where it is reinforced by the target strip.

The age stability of the decrease in release characteristics of the release coating of the target strip, as caused by exposure to the ionizing plasma, is important due to the fact that the diapers of the present invention might be used at various times after production. The ionizing plasma can be provided by a conventional electrical discharge corona or a flame.

The method of the present invention includes the steps of unwinding a pressure-sensitive adhesive reinforcing tape having a polymeric backing sheet material bearing a pressure-sensitive adhesive on one side of the backing sheet and a hydrophobic polyvinyl carbamate release coating on the other side of the backing sheet material; exposing the release coating to ionizing plasma; cutting the reinforcing tape into target strips; providing a substrate sheet material; and adhering the pressure-sensitive adhesive bearing side of the target strips to the substrate.

The amount of ionizing plasma provided must be sufficient to effect the change in the surface of the hydrophobic polyvinyl carbamate release coating which results in the increase in adhesion. The amount of ionizing plasma required to provide the desired increase in peel adhesion is dependent on the adhesive used on the fastening tape tab. Generally, when the fastening tape tab has an adhesive having a higher glass transition temperature which generally results in a stiffer adhesive, a greater increase in peel value can be seen than when the adhesive has a lower glass transition temperature. When the ionizing plasma is provided by a corona treater, energy densities as low as 0.1 $J/cm^2$ or less can provide the desired increase in adhesion when the fastening tape tab adhesive has a higher glass transition temperature, e.g., above about 262° K. When the fastening tape tab adhesive has a lower glass transition temperature, e.g., below about 257° K., energy densities of 0.4 J/cm² or more may be required to provide the desired effect. Generally, the energy density should be less than that which degrades the substrate of the target strip. When the substrate of the target strip is polypropylene, the energy density is preferably not in excess of 1.2 J/cm².

In the drawings similar elements are referred to by the same number. FIG. 1 is a schematic representation of the portion of a manufacturing line for producing disposable garments, such as disposable diapers, in which target strips 20 of a pressure-sensitive adhesive reinforcing tape 11 are attached to a substrate 22 which forms the outer layer of the disposable garment. In FIG. 1 the pressure-sensitive adhesive reinforcing tape 11 is supplied from supply roll 10. Pressure-sensitive adhesive reinforcing tape 11 comprises a polymeric backing 13, a pressure-sensitive adhesive 14, and a release coating 12. The pressure-sensitive adhesive reinforcing tape 11 is guided through corona treater 15 by driven guide rolls 16 resulting in treated release coating 17.

The pressure-sensitive adhesive reinforcing tape 11, with corona treated release coating 17, is then guided onto the surface of vacuum wheel 18 where it is cut into target strips 20 by action of cutting wheel 19. The substrate 22 which is to become the outer layer of the disposable diaper is supplied from supply roll 21 and is guided by guide roll 23. Target strip 20 of pressure-sensitive adhesive reinforcing tape 11, with corona treated release coating 17 is laminated to substrate 22 by vacuum wheel 18 pressing target strip 20 to substrate 22. Pressure is applied to facilitate this lamination by backup roll 24. Target strip 20 of pressure-sensitive adhesive reinforcing tape 11, with treated release coating 17, is held to substrate 22 by the pressure-sensitive adhesive 14 of target strip 20. The pressure-sensitive adhesive reinforcing tape 11 is removed from supply roll 10 by action of driven guide rolls 16 at a speed lower than that of substrate 22 which allows for target strip 20 to be applied to substrate 22 at spaced apart locations. The circumferential speed of vacuum wheel 18 approximately corresponds to that of substrate 22. The speed of the pressure-sensitive adhesive reinforcing tape 11 is less than that of substrate 22 thus allowing for the positioning of target strip 20 at spaced apart locations on substrate 22. For a more detailed description of vacuum wheel type applicators see U.S. Pat. No. 3,750,511, which is incorporated herein by reference.

In manufacturing disposable garments, such as disposable diapers, with the method of the present invention it is desirable that the level of exposure of the release coating to the ionizing plasma be held constant through line speed changes as are encountered during line start-up and shut-down. To achieve this, a means can be provided for controlling the power output of the corona treater. When electrical discharge corona is used to provide the ionizing plasma such means can involve a voltage control. A means for automatically controlling the power output in response to the speed of the substrate 20 can also be provided. Such means could be provided by a feedback loop which monitors the substrate speed and controls the output power in response to this speed.

FIG. 2 shows the corona treater 15 in greater detail. In FIG. 2, pressure-sensitive adhesive reinforcing tape 11 is shown as it passes through corona treater 15 with release coating 12 exposed to the corona discharge 27 created by an electrical discharge between active corona electrode 26 and ground roll 25. The release coating 12 of pressure-sensitive adhesive reinforcing tape 11 faces active corona electrode 26 when passing through the corona treater 15 and is converted to treated release coating 17 by exposure to corona discharge 27. The pressure-sensitive adhesive 14 of pressure-sensitive adhesive reinforcing tape 11 contacts ground roll 25 as it passes through corona treater 15.

FIG. 3 is an expanded view of a target strip 20 of pressure-sensitive adhesive reinforcing tape 11 with corona treated release coating 17. The target strip 20 is shown adhered to substrate 22 through pressure-sensitive adhesive 14 which is carried on backing film 13.

FIG. 4 shows a disposable diaper 28 prepared by the method of the present invention, laid flat with outer layer 29 facing up. A target strip 20 of a pressure-sensitive adhesive reinforcing tape with a corona treated surface 17 is adhered to outer layer 29 Disposable diaper 28 has pressure-sensitive adhesive fastening tape tabs 30 with pressure-sensitive adhesive 31, which are used to fit the diaper to a wearer by adhering tabs 30 to corona treated release surface 17 of target strip 20 of pressure-sensitive adhesive reinforcing tape which is adhered to the outer layer 29 of diaper 28.

Figure 5:
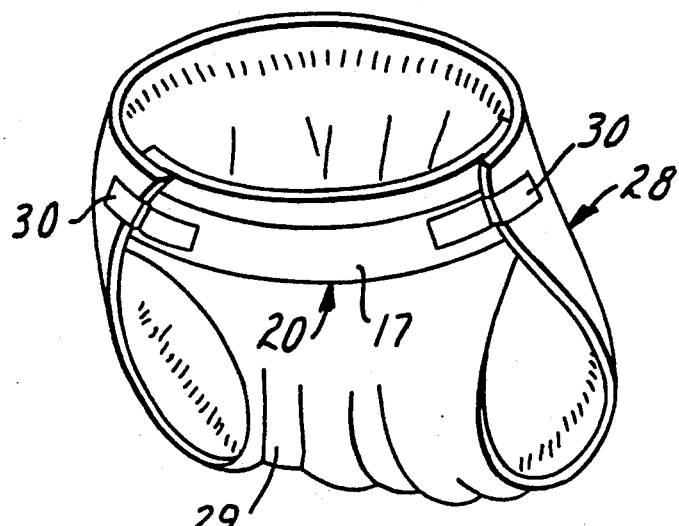
FIG. 5 is a perspective view of a disposable diaper accordance with one aspect of the invention.

FIG. 5 is a perspective view of disposable diaper 28 in which pressure-sensitive adhesive fastening tape tabs 30 are adhered to corona treated release coating 17 of a target strip 20 of a pressure-sensitive adhesive reinforcing tape which is adhered to outer layer 29 of diaper 28.

The following examples illustrate the invention and are not intended to limit the scope thereof. In the examples, all parts and percentages are by weight unless otherwise indicated.

In the examples, the following test methods are used:

135° Peel Adhesion

Testing is carried out at constant temperature (23±2° C.) and humidity (50±2% relative humidity) using a constant rate extension Instron TM tensile tester with a 135° test jig secured in the lower jaw. The reinforcing strip to be tested (5×12.5 cm) is adhered by a pressure-sensitive adhesive transfer tape to a steel panel. After attaching a 20 cm paper leader to a 2.54 cm wide pressure-sensitive adhesive fastening tape tab, the tab is centered over the reinforcing strip, adhesive side down, and immediately rolled lengthwise with one pass in each direction of a mechanically operated 4.5 lb (2.04 kg) hard-rubber roller. The adhesive on the tab Type A is a mixture containing 43 weight percent Kraton TM 1107 (an A-B-A block copolymer of styrene and isoprene available from Shell Chemical Company), 37.5 weight percent Escorez TM 1310 (a solid tackifying resin available from Exxon Chemical Company), 18.5 weight percent Zonarez TM A-25 (a liquid tackifying resin available from Arizona Chemical Company), and 1 weight percent Irganox TM 1076 (an antioxidant available from Ciba-Geigy Corporation) and has a glass transition temperature of 254.9° K. and a coating weight of 40 g/m². The adhesive on the tab Type B is a mixture containing 33 weight percent Kraton TM 1107, 46.9 weight percent Escorez TM 1310, 19.1 weight percent Zonarez TM A-25, and 1 weight percent Irganox TM 1076 and has a glass transition temperature of 263.7° K. and a coating weight of 50 g/m². Within 15 seconds, the panel is slid into the jig slot, and the leader is clamped into the upper jaw, and the fastening tab is peeled back using a chart speed of 12.5 cm/minute and a crosshead speed of 30 cm/minute. The peel value is read from the chart, disregarding the portion of the trace due to removal of the initial and final 0.63 cm of the tab. When the peel is shocky, i.e., erratic, an average value between the peaks and valleys of the trace is read.

EXAMPLES 1-5 AND COMPARATIVE EXAMPLE C1

In Example 1, one face of a biaxially oriented polypropylene film having a thickness of about 25.4 micrometers and smooth surfaces on both sides was gravure coated with a polyvinyl N-octadecyl carbamate solution (2.5 weight percent solids in 86 parts heptane, 11 parts xylene, and 3 parts isopropyl alcohol) prepared as described in U.S. Pat. No. 2,532,011. The coating was dried at 38° C. for 2.5 minutes to provide a dried release coating weighing 0.11 g/m². The other face of the film was coated with a pressure-sensitive adhesive (50 weight percent Kraton TM 1107, an A-B-A linear block copolymer of styrene and isoprene available from Shell Chemical Company, 49 weight percent Wingtack TM Plus, a solid tackifying agent available from the Goodyear Chemical Company, and 1 weight percent Irganox TM 1076, an antioxidant available from Ciba-Geigy Corporation) at a weight of 16.75 g/m². The resulting pressure-sensitive adhesive reinforcing tape was then wound in roll form and the roll was cut to 22.2 cm width to provide a supply roll.

This supply roll was placed on a production line similar to that shown in FIG. 1. The tape was passed through a 500W-500 series corona treater available from Pillar Corporation and having a Coronalok TM II power supply, available from ENI Power Systems, Inc., at a rate of 20 m/min using a net power level of 225 watts with a distance between the active corona electrode and the release coating to provide an energy density of 0.2 J/cm². The tape was cut to form target strips which were adhered to a polyethylene film substrate.

In Examples 2 to 5, pressure-sensitive reinforcing tape was prepared as in Example 1. The release coating was treated by exposure to an electrical discharge corona as in Example 1 using the net power levels and line speeds set forth in Table 1. The resulting energy densities are also reported in Table 1. The tape was cut and the target strips thus formed were adhered to the polyethylene substrate. In Comparative Example C1, the release coating was not exposed to corona treatment but other processing steps were the same as in Examples 1-5.

Each tape was tested for initial adhesion and adhesion after aging at about 50° C. for 15 days using the 135° Peel Adhesion Test with test tab Type A. Each tape was also tested for readhesion by repeating the test using the same test area on the treated release coating and the same adhesive fastening tab. The results are set forth in Table 2.

TABLE 1

| Example | Power level (watts) | Line speed (m/min) | Energy density (J/cm²) |
|---|---|---|---|
| 1 | 225 | 20 | 0.2 |
| 2 | 450 | 20 | 0.4 |
| 3 | 1200 | 20 | 0.8 |
| 4 | 1050 | 15 | 1.2 |
| 5 | 950 | 10 | 1.6 |

TABLE 2

| | 135° Peel adhesion (g/2.54 cm width) | | | |
|---|---|---|---|---|
| Example | Initial | Initial readhesion | Aged | Aged readhesion |
| C1 | 325* | 335* | 215* | 205* |
| 1 | 570** | 450** | 455 | 400 |
| 2 | 610 | 420 | 575 | 465 |
| 3 | 900 | 495 | 840 | 565 |
| 4 | 880 | 415 | 825 | 565 |
| 5 | 895 | 445 | 915 | 615 |

*shocky, i.e., nonuniform peel
**slightly shocky

As can be seen from the data in Tables 1 and 2, treatment of the polyvinyl N-octadecyl carbamate coated biaxially oriented target strip with energy densities as low as 0.2 J/cm² provide an increase in 135° peel adhesion and good readhesion when tested with test tab Type A.

EXAMPLES 6 TO 10 AND COMPARATIVE EXAMPLE C2

In Examples 6 to 10, pressure-sensitive adhesive reinforcing tape was prepared, corona treated, formed into target strips and adhered to the substrate as in Examples 1 to 5, respectively. In Comparative Example C2, the release coating was not exposed to corona treatment.

Each tape was tested as in Examples 1 to 5 except that test tab Type B was used. The results are set forth in Table 3.

TABLE 3

| | 135° Peel adhesion (g/2.54 cm width) | | | |
|---|---|---|---|---|
| Example | Initial | Initial readhesion | Aged | Aged readhesion |
| C2 | 125* | 135* | 75* | 85* |
| 6 | 910* | 730* | 430* | 430* |
| 7 | 860* | 810* | 380* | 410* |
| 8 | 1105* | 845** | 790** | 800** |
| 9 | 1175* | 705** | 745** | 810** |
| 10 | 1075* | 695* | 825** | 850** |

*shocky, i.e., nonuniform peel
**slightly shocky

As can be seen from the data in Table 3, corona treatment increase the 135° peel adhesion. In comparing the data in Tables 2 and 3, it can be seen that the corona treatment provides a greater increase in 135° peel adhesion with the more aggressive test tab Type B used in Examples 6-10 than with less aggressive test tab Type A used in Examples 1-5.

EXAMPLES 11 TO 14 AND COMPARATIVE EXAMPLES C3 and C4

In Examples 11 to 14 and Comparative Examples C3 and C4, an ethylene/propylene film cast from WRS-7-319 available from Shell Chemical Company and having a thickness of about 56 micrometers and matte surfaces on each side was coated with a polyvinyl N-octadecyl carbamate solution (5 weight percent solids in 69.5 parts heptane, 27.3 parts xylene, and 3.2 parts isopropyl alcohol) and dried as in Example 1 to provide a dried release coating weighing 0.39 g/m². The other face of the film was coated with a pressure-sensitive adhesive (35 weight percent Kraton TM 1107, 47.5 weight percent Wingtack Plus TM, 16.5 weight percent Wingtack TM 10, a liquid tackifying agent available from Goodyear Chemical Company, and 1 weight percent Irganox TM 1076) at a weight of 20.9 g/m², and formed into a supply roll of reinforcing tape as in Example 1.

The release coating face of the reinforcing tapes of Examples 11-14 and Comparative Example C4 was treated by exposure to an electrical discharge corona as in Example 1 using the power levels and line speeds set forth in Table 4. The resulting energy densities are also reported in Table 4. The treated reinforcing tape was cut to form target strips which were adhered to the polyethylene substrate as in Example 1. In Comparative Example C3, the release coating was not exposed to corona treatment.

Each tape was tested for 135° peel adhesion as in Example 1. The results are set forth in Table 5.

TABLE 4

| Example | Power level (watts) | Line speed (m/min) | Energy density (J/cm$^2$) |
| --- | --- | --- | --- |
| C4 | 225 | 20 | 0.2 |
| 11 | 450 | 20 | 0.4 |
| 12 | 1200 | 20 | 0.8 |
| 13 | 1050 | 15 | 1.2 |
| 14 | 950 | 10 | 1.6 |

TABLE 5

| | 135° Peel adhesion (g/2.54 cm width) | | | |
| --- | --- | --- | --- | --- |
| Example | Initial | Initial readhesion | Aged | Aged readhesion |
| C3 | 570 | 480 | 500 | 425 |
| C4 | 660 | 570 | 595 | 495 |
| 11 | 1145 | 795 | 770 | 620 |
| 12 | 1090 | 810 | 730 | 610 |
| 13 | 1040 | 805 | 600 | 520 |
| 14 | 1070 | 800 | 910 | 710 |

As can be seen from the data in Table 5, the corona treatment increased the 135° peel adhesion and provided good readhesion of test tab Type A to the release coated ethylene/propylene copolymer at energy densities as low as 0.4 J/cm$^2$. Comparative Example C4 demonstrates that with the ethylene/propylene substrate in the target strip and the softer, less aggressive test tab Type A, an energy density of 0.2 J/cm$^2$ is insufficient to provide the desired increase in 135° peel adhesion. The 135° peel adhesion values are somewhat lower when using the biaxially oriented polypropylene film with the tape tab Type A (Examples 1-5) than when the cast ethylene/propylene copolymer film was used with test tab Type A (Examples 11-14).

EXAMPLES 15 TO 19 AND COMPARATIVE EXAMPLE C5

In Examples 15 to 20, pressure-sensitive adhesive reinforcing tape was prepared, corona treated, formed into target strips and adhered to the substrate as in Examples 11 to 15, respectively. In Comparative Example C5, the release coating was not exposed to corona treatment.

Each tape was tested as in Example 1, except that test tab Type B was used. The results are set forth in Table 6.

TABLE 6

| | 135° Peel adhesion (g/2.54 cm width) | | | |
| --- | --- | --- | --- | --- |
| Example | Initial | Initial readhesion | Aged | Aged readhesion |
| C5 | 495* | 520* | 365* | 375* |
| 15 | 920* | 810* | 530* | 515* |
| 16 | 1965 | 1480 | 1045** | 1030** |
| 17 | 1860 | 1340 | 1425 | 1160 |
| 18 | 1750 | 1400 | 930** | 930** |
| 19 | 1760 | 1400 | 1535 | 1280 |

*shocky, i.e., nonuniform peel
**slightly shocky

As can be seen from the data in Table 6, the corona treatment increased the 135° peel adhesion values and provided good readhesion. Again, test tab Type B (Examples 5-19) provided higher 135° peel adhesion values than did test tab Type A (Examples 11-14) and the biaxially oriented polypropylene film provided higher 135° peel adhesion values than did the cast ethylene/propylene copolymer film.

The various modifications and alterations of this invention will be apparent to those skilled in the art without departing from the scope and spirit of this invention and this invention should not be restricted to that set forth herein for illustrative purposes.

What is claimed is:

1. A disposable article having a fastening means comprising a film substrate having a target strip and a fastening tape, said target strip comprising a backing film having a first pressure-sensitive adhesive on one face thereof adhered to the film substrate and on the other face thereof a release coating of hydrophobic polyvinyl carbamate, said fastening tape having a second pressure-sensitive adhesive on one face thereof for adhesion to the target strip, the target strip release coating having been subjected to ionizing plasma treatment such that the fastening tape has an increase in 135° peel adhesion to the target strip of at least about 50% over an untreated target strip and which increased adhesion does not decrease more than 60% after storage at about 50° C. for 15 days.

2. The disposable article of claim 1 wherein said backing film is formed from thermoplastic material.

3. The disposable article of claim 2 wherein said thermoplastic material is polyester, polyethylene, polypropylene, or a copolymer of propylene and ethylene.

4. The disposable article of claim 1 wherein said backing film is biaxially oriented polypropylene and said 135° peel adhesion of said fastening tape to said target strip is greater than about 400 g/2.54 cm width.

5. The disposable article of claim 1 wherein said backing film is cast from an ethylene/polypropylene copolymer and said 135° peel adhesion of said fastening tape to said target strip is greater than about 600 g/2.54 cm width.

6. The disposable article of claim 1 wherein said backing film is between about 20 and 50 micrometers thick.

7. The disposable article of claim 1 wherein said first adhesive is a tackified synthetic rubber.

8. The disposable article of claim 7 wherein said rubber is a block copolymer elastomer.

9. The disposable article of claim 1 wherein said hydrophobic polyvinyl carbamate has nitrogen bonded hydrocarbon side chains which provide terminal alkyl groups of more than five carbon atoms.

10. The disposable article of claim 1 wherein said, hydrophobic polyvinyl carbamate is present in an amount of about 0.02 to 1.2 g/m$^2$.

11. A method for producing disposable articles comprising the steps of (a) unwinding a pressure-sensitive adhesive reinforcing tape having a polymeric backing sheet material bearing a pressure-sensitive adhesive on one side of said backing sheet material and a release coating on the other side of said backing sheet material;

(b) exposing said release coating to ionizing plasma;

(c) cutting said reinforcing tape into target strips;

(d) providing a substrate sheet material; and (e) adhering said pressure-sensitive adhesive bearing side of said target strips to said substrate, said exposed release coating having an increase in adhesion to pressure-sensitive adhesive of at least about 50% over an untreated target strip and which increased adhesion does not decrease more than 60% after storage at 50° C. for 15 days.

12. The method of claim 11 wherein said ionizing plasma is corona discharge.

13. The method of claim 12 wherein said corona discharge is provided in an amount of at least about 0.05 J/cm$^2$.

14. The method of claim 12 wherein said corona discharge is provided in an amount of at least 0.2 J/cm$^2$.

15. A disposable diaper comprising a porous facing layer to be positioned adjacent an infant's skin, an absorbent batt, a water-impervious backing sheet having a target strip and a fastening tape, said target strip comprising a backing film having a first pressure-sensitive adhesive on one face thereof adhered to the film substrate and on the other face thereof a release coating of hydrophobic polyvinyl carbamate, said fastening tape having a second pressure-sensitive adhesive on one face thereof for adhesion to the target strip, the target strip release coating having been subjected to ionizing plasma treatment such that the fastening tape has an increase in 135° peel adhesion to the target strip of at least about 50% over an untreated target strip and which increased adhesion does not decrease more than 60% after storage at about 50° C. for 15 days.

* * * * *